United States Patent
Rothschild et al.

(10) Patent No.: US 6,218,530 B1
(45) Date of Patent: Apr. 17, 2001

(54) COMPOUNDS AND METHODS FOR DETECTING BIOMOLECULES

(75) Inventors: Kenneth J. Rothschild, Newton; Jerzy Olejnik, Brookline, both of MA (US)

(73) Assignee: AmberGen Inc., Boston, MA (US)

( * ) Notice: Subject to any disclaimer, the term of this patent is extended or adjusted under 35 U.S.C. 154(b) by 0 days.

(21) Appl. No.: 09/323,424

(22) Filed: Jun. 1, 1999

Related U.S. Application Data (60) Provisional application No. 60/087,641, filed on Jun. 2, 1998.

(51) Int. Cl.[7] .............................. C12Q 1/68; C07H 19/00; C07H 21/00; C07H 21/02; C07H 21/04
(52) U.S. Cl. ...................... 536/25.32; 435/6; 536/22.1; 536/23.1; 536/24.3; 536/24.33; 536/25.3
(58) Field of Search ............................... 435/6; 536/22.1, 536/23.1, 26.2, 24.33, 25.3, 25.32

(56) References Cited

U.S. PATENT DOCUMENTS

| | | | |
|---|---|---|---|
| 5,643,722 | 7/1997 | Rothschild et al. | 435/6 |
| 5,922,858 | 7/1999 | Rothschild et al. | 536/24.1 |
| 5,948,624 | 9/1999 | Rothschild et al. | 435/6 |
| 5,986,076 | 11/1999 | Rothschild et al. | 536/22.1 |
| 6,057,096 | 5/2000 | Rothschild et al. | 435/6 |

OTHER PUBLICATIONS

Agrawal, S., Christodoulu, C., and Gait, M., "Efficient Methods For Attaching Non–Radioactive Label To The 5' Ends Of Synthetic Oligodeoxyribonucleotides," *Nucleic Acids Research* vol. 14 No. 15 pp. 6227–6245 (1986).

Bannwarth, W. and Wippler, J., "110. A new Combined Purification/Phosphorylation Procedure For Oligodeoxynucleotides," *Helvetica Chimica Acta*, vol. 73, pp. 1139–1147 (1990).

Beaucage, S. and Radhakrishnan, P., "The Functionalization Of Oligonucleotides Via Phosphoramidite Derivatives," *Tetrahedron* vol. 49, No. 10. pp. 1925–1963 (1993).

Gildea, B., Coull, J., and Koster, H., "A Versatile Acid–Labile Linker For Modification Of Synthetic Biomolecules," *Tetrahedron Letters*, vol. 31, No. 49, pp. 7095–7098 (1990).

Leikauf, E., Barnekow, F., and Koster, H., "Heterobifunctional Trityl Derivatives As Linking Reagents For The Recovery Of Nucleric Acids After Labeling And Immobilization," *Tetrahedron* vol. 51 No. 13, pp. 3793–3802 (1995).

Nelson, P., Frye R., and Edison, L., Bifunctional Oligonucleotide Probes Synthesized Using A Novel CPG Support Are Able To Dectect Single Base Pair Mutations Nucleic Acids Research, vol. 17 No. 18, pp. 7187–7195 (1989).

Nelson, P., Kent, M., and Muthini, S., "Oligonucleotide Labeling Methods 3. Direct Labeling Of Oligonucleotides Employing A Novel, Non–Nucleosidic, 2–Aminobutyl–1, 3–Propanediol Backbone," *Nucleic Acids Research* vol. 20 No.23, pp. 6253–6259 (1992).

Nelson, P., Sherman–gold, R., and Leon, R., "A New And Versatile Reagent For Incorporating Mutiple Primary Aliphatic Amines Into Synthetic Oligonucleotides," *Nucleic Acids Research* vol. 17 No. 18, pp. 7179–7186 (1989).

Olejnik, J., Krymanska–Olejnik, E., and Rothschild, K., "Photocleavable Biotin Phosphoramidite For 5'–End–Labeling, Affinity Purification And Phosphorylation Of Synthetic Oligonucleotides," *Nucleic Acids Research* vol. 24 No. 2, pp. 361–366 (1996).

*Primary Examiner*—Jezia Riley
(74) *Attorney, Agent, or Firm*—Medlen & Carroll, LLP (57) ABSTRACT

Methods are described for synthesizing compounds useful for detecting nucleic acids, and in particular, the hybridization of nucleic acids. Photocleavable agents are described, including but not limited to photocleavable nucleotides and photocleavable phosphoramidites.

12 Claims, 9 Drawing Sheets

COMPOUNDS AND METHODS FOR DETECTING BIOMOLECULES

This application for patent under 35 U.S.C. 111(a) claims priority to Provisional Applications Ser. Nos. 60/087,641 filed Jun. 2, 1998 under 35 U.S.C. 111(b).

This invention was made with government support under grants from the National Institutes of Health (GM54920-01) and the Army Research Office (ARO-DAAH04-96-C-0050). The government has certain rights in the invention.

FIELD OF THE INVENTION

The present invention relates to compounds and methods for detecting biomolecules, and in particular, the detection of nucleic acid and nucleic acid hybridization using photocleavable phosphoramidites.

BACKGROUND

Numerous methods have been developed for the incorporation of ligands into synthetic oligonucleotides using phosphoramidite chemistry. See S. L. Beaucage and P. I. Radhakrishnan, *Tetrahedron* 49:1925 (1993). One approach is based on the incorporation of an aliphatic amino group into synthetic oligonucleotides by use of an amino-modifier phosphoramidites or modified CPGs. See S. Agrawal et al., *Nucleic Acids Res.,* 14: 6227 (1986). See P. S. Nelson et al., *Nucleic Acids Res.* 20:6253 (1992); P. S. Nelson et al., *Nucleic Acids Res.* 17:7179 (1989); P. S. Nelson et al., *Nucleic Acids Res.* 17: 7187 (1989). Such amino groups allow the post-synthetic addition of a variety of molecules including fluorescent markers, biotin, haptens or enzymes which can be used as hybridization probes for non-radioactive detection of specific target DNA/RNA or as sequencing primers. Amino-modified oligonucleotides have also been used for preparation of affinity matrices and as immobilized PCR primers.

One disadvantage of covalent labeling and immobilization of oligonucleotides is that the covalent bond is not selectively cleavable, and, therefore does not allow for the recovery/release of oligonucleotide or the removal of the label. In order to circumvent this problem, several approaches have been proposed based on chemical cleavage. These include the use of cleavable disulfide bonds or the introduction of acid cleavable linkers. See W Bannwarth and J. Wippler, *Helv. Chim. Acta* 73:1139 (1990); B. D. Gildea et al., *Tetrahedron Lett.* 31:7095 (1990); E.Leikauf et al., *Tetrahedron* 51:3793 (1995); J. Olejnik et al., *Nucleic Acids Res.* 24: 361 (1996). These approaches, however, require the application of chemical reagents that are not suitable for many applications. They also necessitate removal of the excess of cleaving reagents and result in residual modification of the oligonucleotide.

SUMMARY OF THE INVENTION

The present invention relates to compounds and methods for detecting biomolecules, and in particular, the detection of nucleic acid and nucleic acid hybridization using photocleavable agents, including photocleavable detectable moieties, photocleavable nucleotides (e.g. photocleavable NTPs) and photocleavable phosphoramidites. It is not intended that the present invention be limited to the type of biomolecule detected. Both nucleic acids and proteins can be detected using the photocleavable agents of the present invention. The details regarding detection of various biomolecules (including proteins) are set forth in Attachments A, B, C, D and E hereto, all of which constitute the disclosure and specification of the present application.

In one embodiment, the present invention contemplates a photocleavable nucleotide. In a specific embodiment, the photocleavable nucleotide is a photocleavable dideoxynucleotide. The latter is useful in a variety of formats and assays, including but not limited to, nucleic acid sequencing.

Figure 2A:
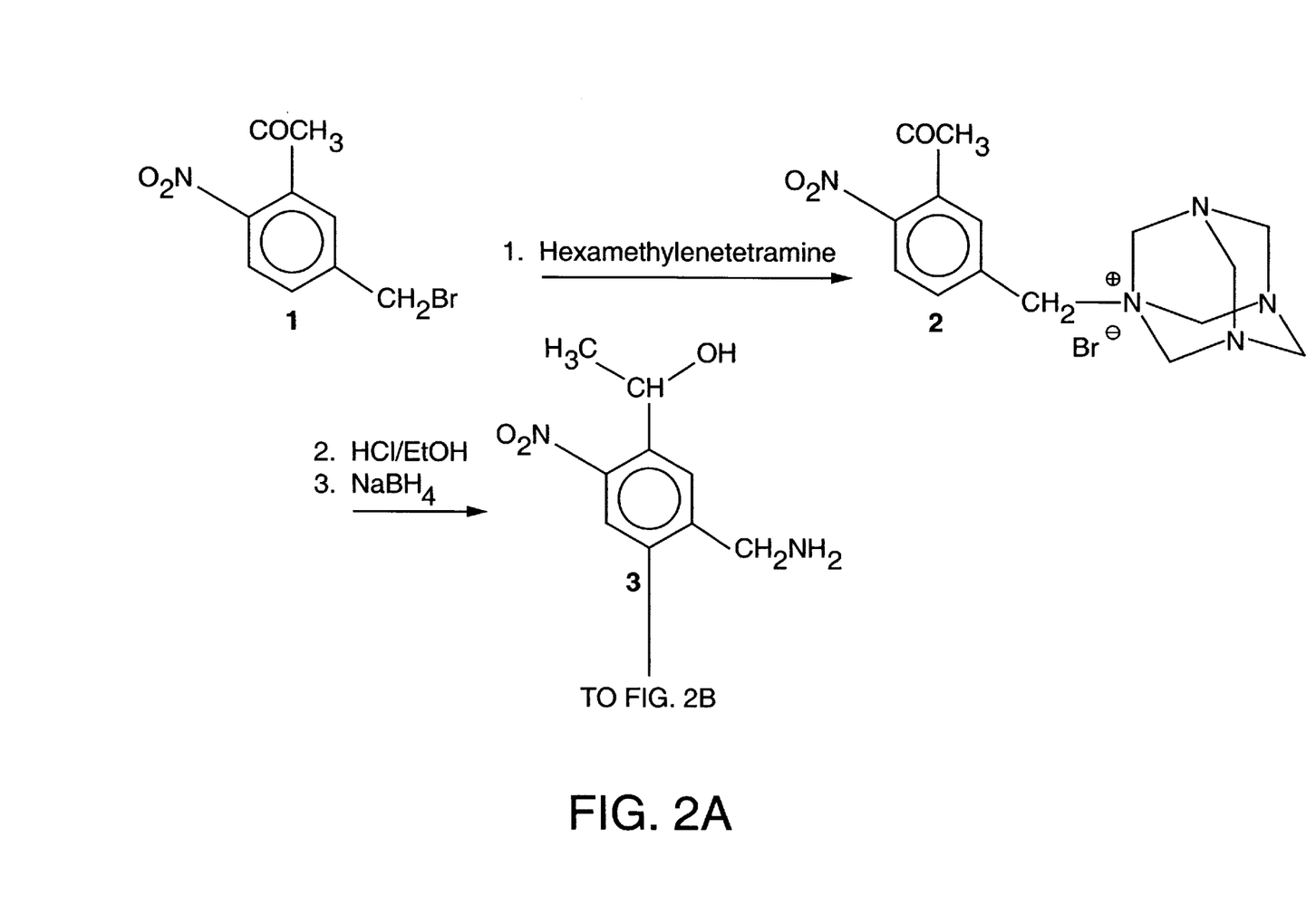
FIGS. 2A and 2B schematically shows one embodiment of a synthesis scheme for a variety of aminotag phosphoramidites of the present invention.
Figure 2B:
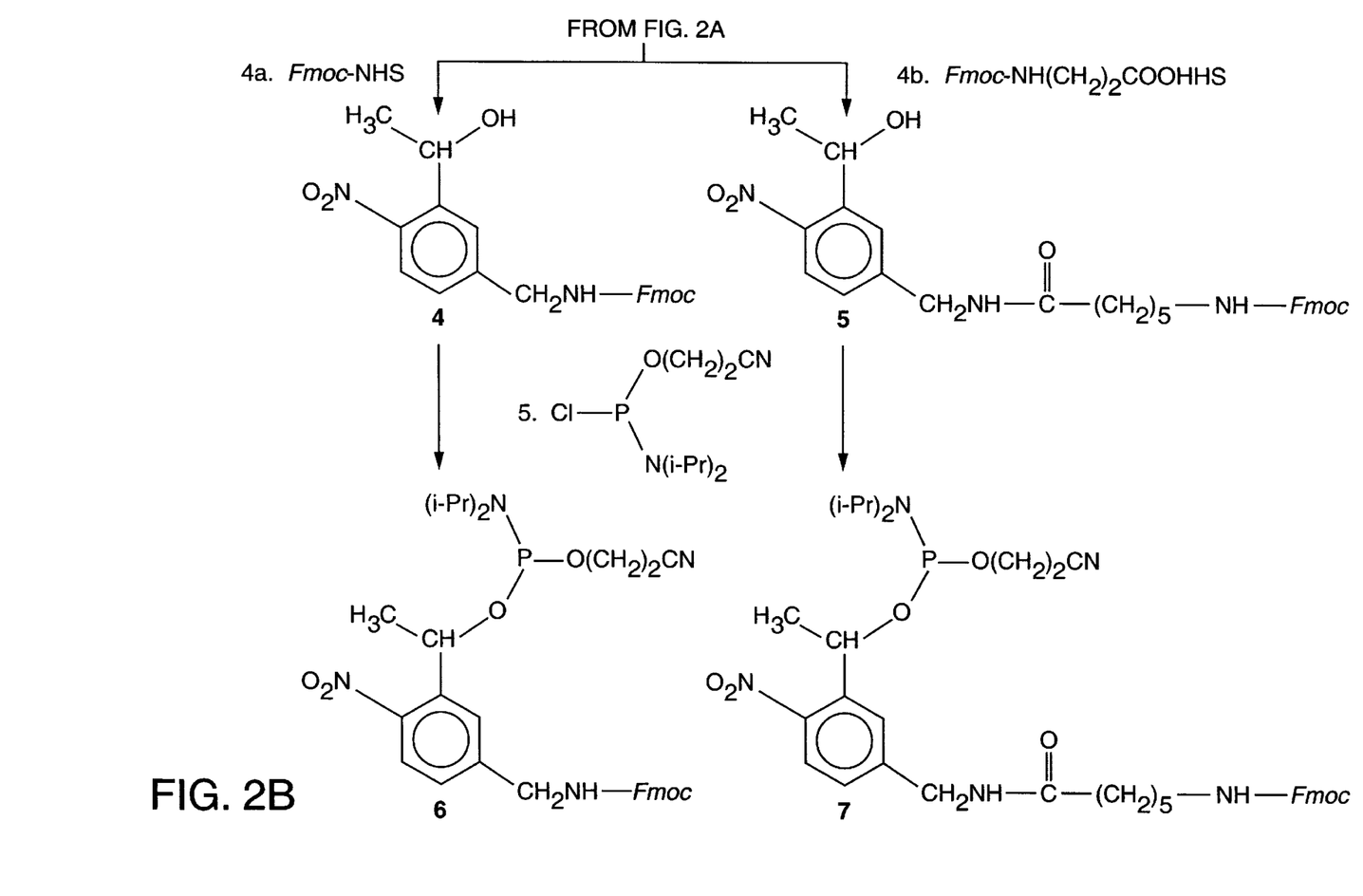

In one embodiment, the present invention contemplates a composition, comprising a photocleavable aminotag phosphoramidite selected from the group consisting of compounds 6 and 7 of FIG. 2B. From FIG. 2B, it should be clear that the present invention contemplates particular protecting groups ("PG") suitable for such compounds, including but not limited to, 9-fluorenylmethoxycarbonyl (FMOC). In a preferred embodiment, the photocleavable aminotag phosphoramidite is incorporated into an oligonucleotide during synthesis at the 5' end of an oligonucleotide.

Figure 4:
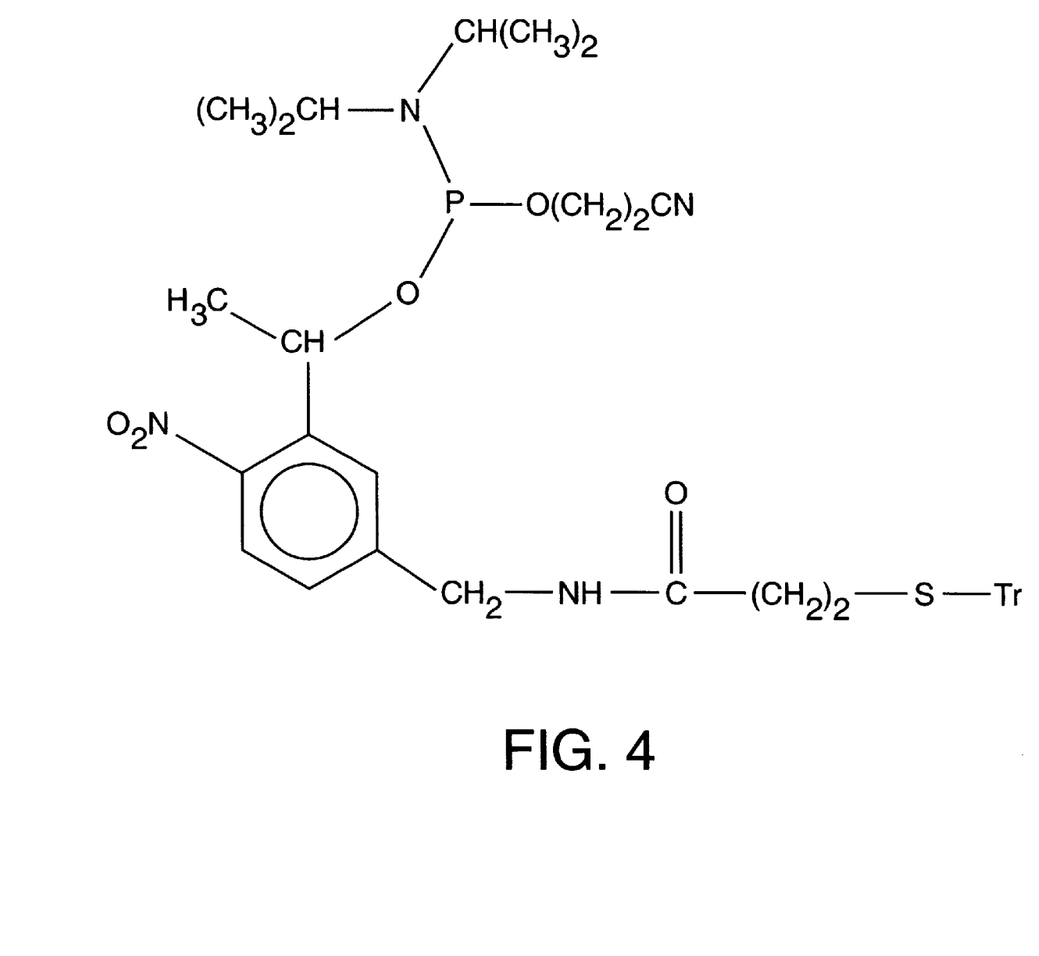
FIG. 4 shows the structure of one embodiment of the sulfhydryltag phosphoramidites of the present invention.

In another embodiment, the present invention contemplates a composition, comprising a photocleavable sulfhydryltag phosphoramidite such as that shown in FIG. 4. In a preferred embodiment, the photocleavable sulfhydryltag phosphoramidite is incorporated at the 5' end of an oligonucleotide.

The present invention also contemplates methods of synthesis of photocleavable phosphoramidites and methods of synthesis of oligonucleotides containing such photocleavable phosphoramidites. Moreover, the present invention contemplates methods of incorporating detectable moieties or markers ("M") to a phosphoramidite and photocleaving so as to release said marker.

In a further embodiment, the present invention contemplates oligonucleotides linked to a solid support or surface via a photocleavable linkage. In such an embodiment, the oligonucleotide can be released from the solid support (e.g. a bead) or a surface (e.g. a gold surface) by photocleavage.

DEFINITIONS

To facilitate understanding of the invention, a number of terms are defined below.

The terms "marker" and "marker molecule" refer to a detectable moiety, i.e. a chemical group, structure of compound that possesses a specifically identifiable physical property which can be distinguished from the physical properties of other chemicals present in the heterologous mixture. It is not intended that the present invention be limited to a particular detectable moiety. For example, the present invention contemplates detectable moieties having the properties of fluorescence, phosphorescence and luminescence. A variety of molecules have such properties as set forth in U.S. application Ser. No. 08/345,807, hereby incorporated by reference. Preferred detectable moieties are those that are detectable by spectrometry, and in particular, by mass spectrometry.

"Nucleic acid sequence" and "nucleotide sequence" as used herein refer to an oligonucleotide or polynucleotide, and fragments or portions thereof, and to DNA or RNA of genomic or synthetic origin which may be single- or double-stranded, and represent the sense or antisense strand.

The photocleavable agents of the present invention can be "linked" or "incorporated" into proteins and nucleic acids. By use of the term "linked" or "incorporated" it is not meant that the entire photocleavable agent need be part of the final molecule. Some photocleavable agents of the present invention have reactive groups (i.e. the agent is an "activated agent") and leaving groups such that the photocleavable agent upon incorporation or linkage loses one or more groups.

The term "portion" when used in reference to a nucleotide sequence refers to fragments of that nucleotide sequence. The fragments may range in size from 1 nucleotide residues (and more preferably 5 or greater) to the entire nucleotide sequence minus one nucleic acid residue. The present invention contemplates, for example, that the photocleavable agents may be incorporated into just a portion of a nucleic acid.

As used herein, the terms "complementary" or "complementarity" are used in reference to "polynucleotides" and "oligonucleotides" (which are interchangeable terms that refer to a sequence of nucleotides) related by the base-pairing rules. For example, for the sequence 5'-AGT-3' is complementary to the sequence 5'-ACT-3'. Complementarity can be "partial" or "total." "Partial" complementarity is where one or more nucleic acid bases is not matched according to the base pairing rules. "Total" or "complete" complementarity between nucleic acids is where each and every nucleic acid base is matched with another base under the base pairing rules. The degree of complementarity between nucleic acid strands has significant effects on the efficiency and strength of hybridization between nucleic acid strands. The present invention contemplates hybridization (e.g. complete, partial, low and high stringency) using oligonucleotides having photocleavable agents incorporated therein.

The terms "homology" and "homologous" as used herein in reference to nucleotide sequences refer to a degree of complementarity with other nucleotide sequences. There may be partial homology or complete homology (i.e., identity). A nucleotide sequence which is partially complementary, i.e., "substantially homologous," to a nucleic acid sequence is one that at least partially inhibits a completely complementary sequence from hybridizing to a target nucleic acid sequence. The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target.

Low stringency conditions comprise conditions equivalent to binding or hybridization at 42° C. in a solution consisting of 5× SSPE (43.8 g/l NaCl, 6.9 g/l $NaH_2PO_4.H_2O$ and 1.85 g/l EDTA, pH adjusted to 7.4 with NaOH), 0.1% SDS, 5× Denhardt's reagent [50× Denhardt's contains per 500 ml: 5 g Ficoll (Type 400, Pharmacia), 5 g BSA (Fraction V; Sigma)] and 100 µg/ml denatured salmon sperm DNA followed by washing in a solution comprising 5× SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol), as well as components of the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

When used in reference to a single-stranded nucleic acid sequence, the term "substantially homologous" refers to any probe which can hybridize (i.e., it is the complement of) to the single-stranded nucleic acid sequence under conditions of low stringency as described above.

As used herein, the term "hybridization" is used in reference to the pairing of complementary nucleic acids using any process by which a strand of nucleic acid joins with a complementary strand through base pairing to form a hybridization complex. Hybridization and the strength of hybridization (i.e., the strength of the association between the nucleic acids) is impacted by such factors as the degree of complementarity between the nucleic acids, stringency of the conditions involved, the $T_m$ of the formed hybrid, and the G:C ratio within the nucleic acids.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (as determined, e.g., by $C_0^t$ or $R_0^t$ analysis) or between one nucleic acid sequence present in solution and another nucleic acid sequence immobilized to a solid support [e.g., a nylon membrane or a nitrocellulose filter as employed in Southern and Northern blotting, dot blotting or a glass slide as employed in in situ hybridization, including FISH (fluorescent in situ hybridization)].

"Stringency" when used in reference to nucleic acid hybridization typically occurs in a range from about $T_m$–5° C. (5° C. below the $T_m$ of the probe) to about 20° C. to 25° C. below $T_m$. The term "$T_m$" is used in reference to the "melting temperature." The melting temperature is the temperature at which a population of double-stranded nucleic acid molecules becomes half dissociated into single strands. As will be understood by those of skill in the art, a stringent hybridization can be used to identify or detect identical polynucleotide sequences or to identify or detect similar or related polynucleotide sequences. Under "stringent conditions" a sequence or fragments thereof will hybridize to the sequence's exact complement and closely related sequences.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotide is referred to as the "5' end" if its 5' phosphate is not linked to the 3' oxygen of a mononucleotide pentose ring. An end of an oligonucleotide is referred to as the "3' end" if its 3' oxygen is not linked to a 5' phosphate of another mononucleotide pentose ring. As used herein, a nucleic acid sequence, even if internal to a larger oligonucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion.

DESCRIPTION OF THE INVENTION

Figure 1:
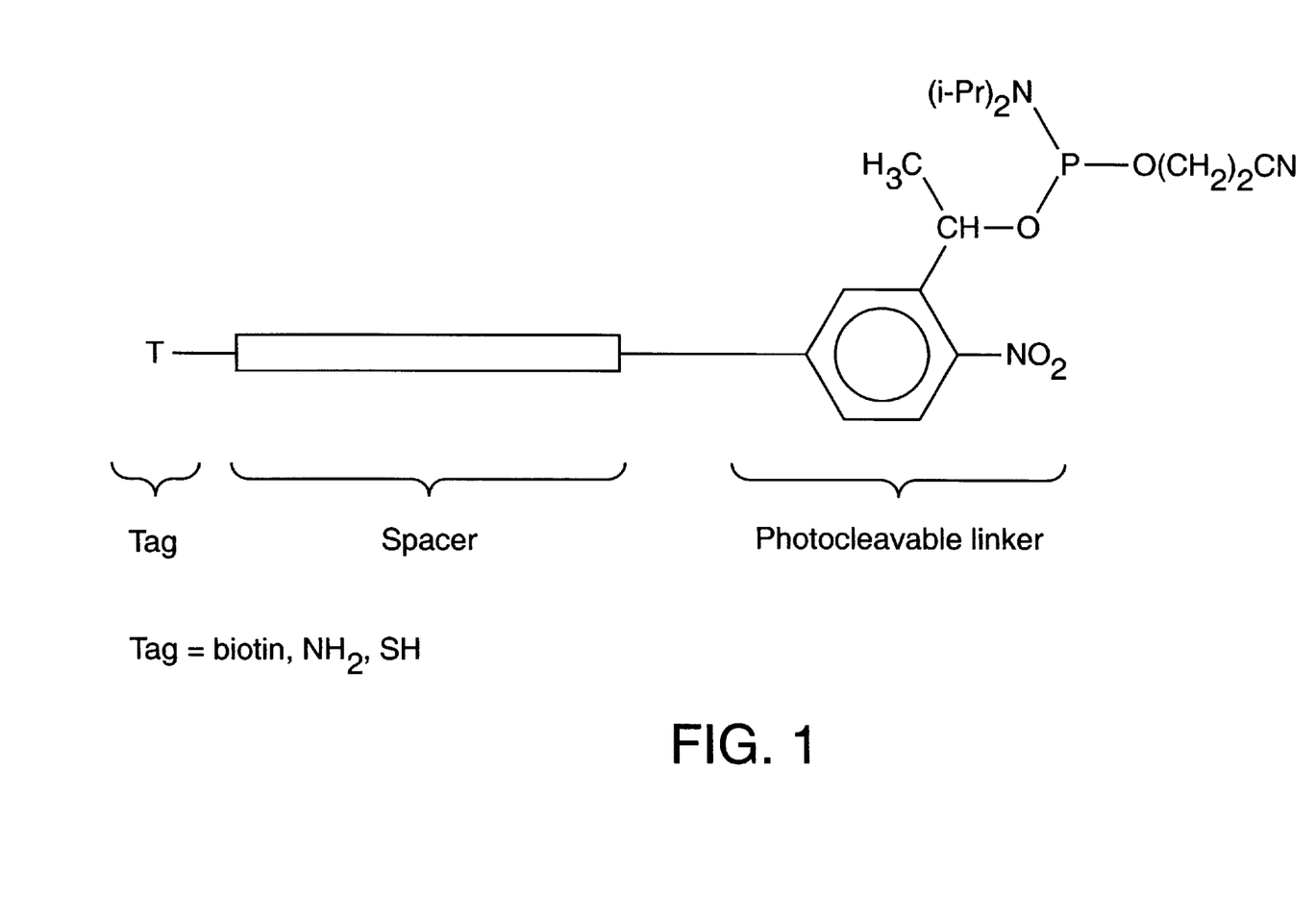
FIG. 1 schematically shows a generic structure for the photocleavable phosphoramidites of the present invention.

The present invention relates to compounds and methods for detecting biomolecules, and in particular, the detection of nucleic acid and nucleic acid hybridization using photocleavable agents, including photocleavable detectable moieties, photocleavable nucleotides and photocleavable phosphoramidites. FIG. 1 schematically shows a generic structure for the photocleavable phosphoramidites of the present invention In one embodiment, the present invention contemplates non-nucleosidic photocleavable phosphoramidites. These reagents introduce a photocleavable amino group on the 5'-terminal phophate of synthetic oligonucleotides and are fully compatible with automated solid support synthesis. The 5' photocleavable amino group enables introduction of a variety of amine-reactive markers onto synthetic oligonucleotides as well as immobilization on activated solid supports. The photocleavable ("PC") bond on the 5'-phosphate can then be selectively cleaved by near-UV illumination thereby enabling release of the marker or detachment of the oligonucleotide from a solid support.

It is not intended that the present invention be limited to the particular marker linked to the 5' terminal phosphate of the oligonucleotide. The preparation of photocleavable conjugates with polypeptides, biotin, digoxigenin, and tetramethylrhodamine are contemplated.

It is specifically contemplated that the 5'-PC-amino group can be used as an affinity tag for photocleavage-mediated affinity purification and phosphorylation of synthetic oligonucleotides in conjunction with activated supports. Upon irradiation with 300–350 nm light, the 5'-PC-amino group is cleaved with high efficiency, resulting in rapid release of 5'-phosphorylated oligonucleotides into solution. Such 5'-PC-arnino labeled oligonucleotides are useful in a variety of applications in molecular biology including multiple non-radioactive probing of DNA/RNA blots, affinity isolation and purification of nucleic acids binding proteins, diagnostic assays requiring release of the probe-target complex or specific marker, cassette mutagenesis and PCR. They enable the spatially-addressable photorelease of the probe-target complexes or marker molecules for diagnostic purposes.

A. Photocleavable AminoTag Phosphoramidites

A variety of aminotag phosphoramidites are contemplated. In one embodiment (FIG. 2B), the PC-aminotag phosphoramidite (compound 6) comprises a protected amino group linked through a methylene group to a photocleavable 1-(2-nitrophenyl)ethyl linker derivatized with N,N'-diisopropyl-2-cyanoethyl phosphoramidite. In another embodiment, the present invention contemplates a "PC-X-aminotag" (FIG. 2B, compound 7) which comprises an additional spacer (e.g. 6-aminocaproic acid, referred to as "X") between the amino group and the photocleavable linker. The properties of modified oligonucleotides prepared using these PC-aminotag phosphoramidites and their conjugates are such that the present invention provides advantages over other cleavable systems (discussed above).

Unlike biotin, which can interact only with avidin/streptavidin coated surfaces, PC-aminotag-phosphoramidite introduces a photocleavable amino group onto the 5' end of an oligonucleotide. As such it can be used to react with a wide variety of activated surfacs and molecules, thereby facilitating the formation of many different PC-linkers and PC-markers.

B. Synthesis of Oligonucleotides With AminoTag Phosphoramidites

Figure 3:
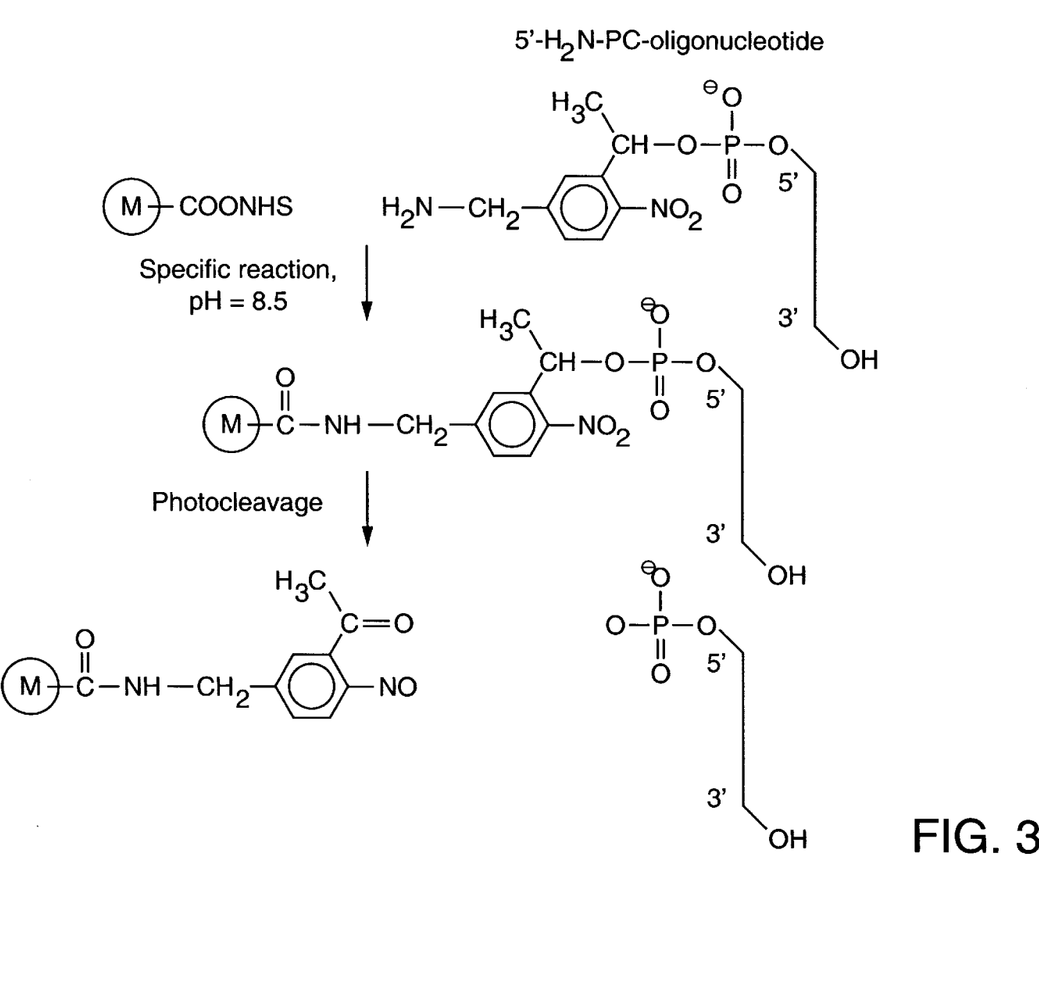
FIG. 3 schematically shows one embodiment of linking a marker ("M") to an aminotag phosphoramidite that has been incorporated into an oligonucleotide, followed by photocleavage.

The photocleavable-aminotag phosphoramidites of the present invention can be readily used in any automated DNA/RNA synthesizer employing standard phosphoramidite chemistry (i.e. an oligonucleotide synthesis means). The selective reaction of PC-aminotag phosphoramidites with the free 5'-OH group of a growing oligonucleotide chain, followed by cleavage from the support and deprotection, results in the introduction of a phosphodiester group linked to a primary aliphatic amino group through a photocleavable linker. This amino group can then be used to introduce a variety of photocleavable markers through a postsynthetic modification reaction (FIG. 3) with amine reactive reagents. It can also be used to attach synthetic oligonucleotides to activated solid supports for a variety of applications requiring immobilization and release of DNA molecules. Upon irradiation with near-UV light, the phosphodiester bond between the photocleavable linker and the phosphate is cleaved, resulting in the formation of a 5'-monophosphate on the released oligonucleotide. The 1-(2-nitrophenyl)ethyl moiety is converted into a 2-nitrosoacetophenone derivative and is released together with the attached marker molecule M.

C. Photocleavable SulfhydrylTag Phosphoramidites

The present invention also contemplates sulfhydryltag phosphoramidites. The design of such compounds (FIG. 4) is similar to that for the aminotag phosphoramidites such that the photocleavable sulfhydryl group can be incorporated at the 5'-end of an oligonucleotide. This phosphoramidite allows for reactions with a variety of thiol-activated supports and biomolecules. A trityl protective group is also incorporated for protection purposes.

D. Photocleavable Phosphoramidites Comprising Peptide Markers

The present invention contemplates photocleavable phosphoramidites comprising peptide markers. Peptides as markers have a number of desirable features when used as mass markers, including a large set of distinct masses which are easily resolved by MALDI-MS. When attached through a photocleavable linker to a specific oligonucleotide sequence, the resulting conjugate can be used in a wide variety of applications in DNA-analysis by mass spectrometry.

Figure 5:
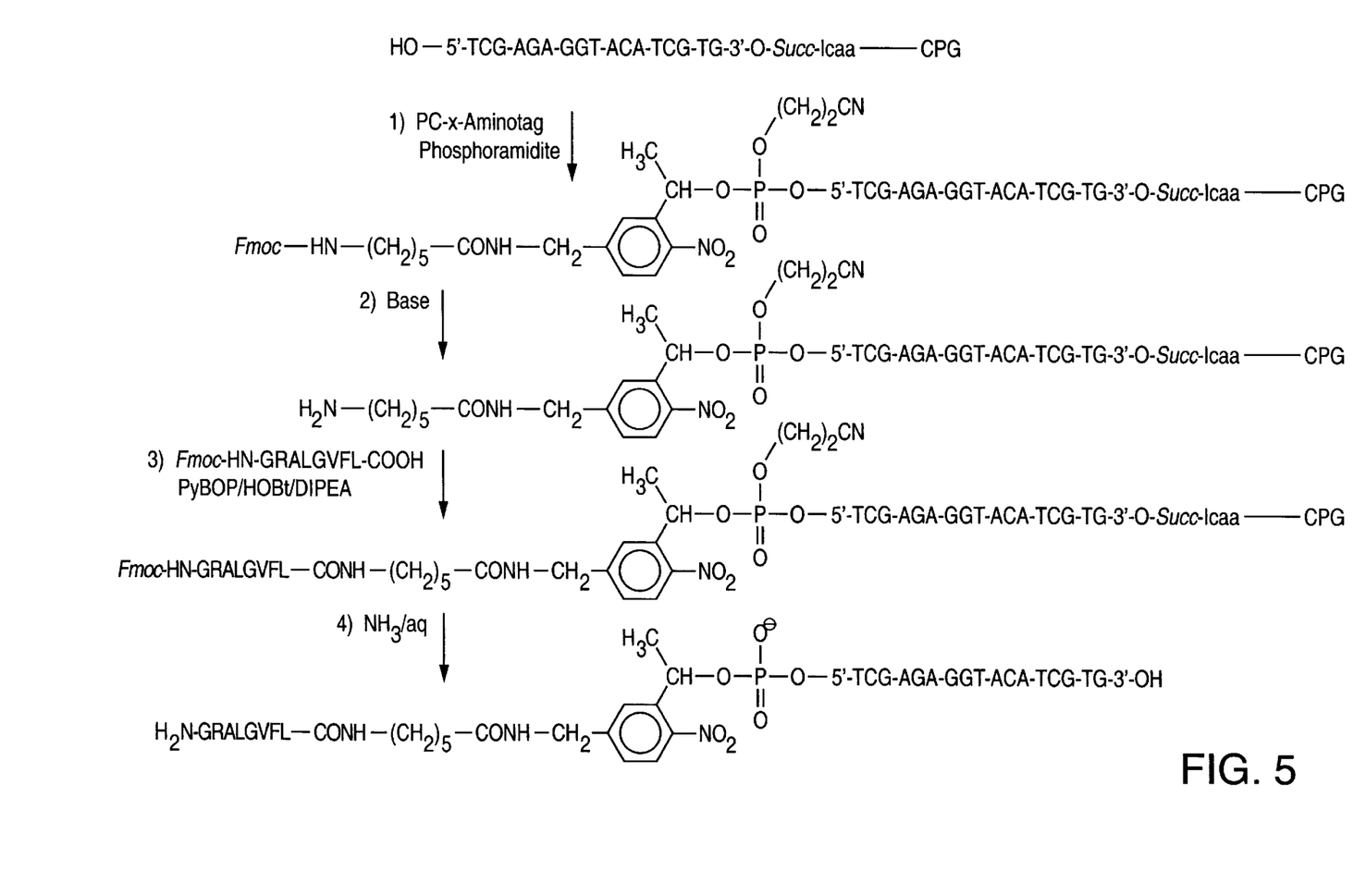
FIG. 5 schematically shows one embodiment of a synthesis scheme for an oligonucleotide conjugate comprising a photocleavable aminotag phosphoramidite and a peptide marker (SEQ ID NO: 1).

The compounds can be made using a conventional solid phase nucleic acid synthesizer (e.g. a synthesis means). The DNA probe is first asembled on an automated DNA synthesizer in the conventional fashion (FIG. 5). The amintotag phosphoramidite is incorporated at the 5' end of the sequence. At the end of the cycle, the support (CPG) is treated with base, which selectively removes the Fmoc protective group from the linker.

In the next step, an N-Fmoc protected peptide marker is introduced and an activating mixture is added, resulting in the formation of the peptide bond between the peptide marker and photocleavable linker DNA. Conventional cleavage and deprotection with ammonia yields the desired conjugate with a free amino group on the peptide marker.

E. Detection Of Peptide Markers

Figure 6:
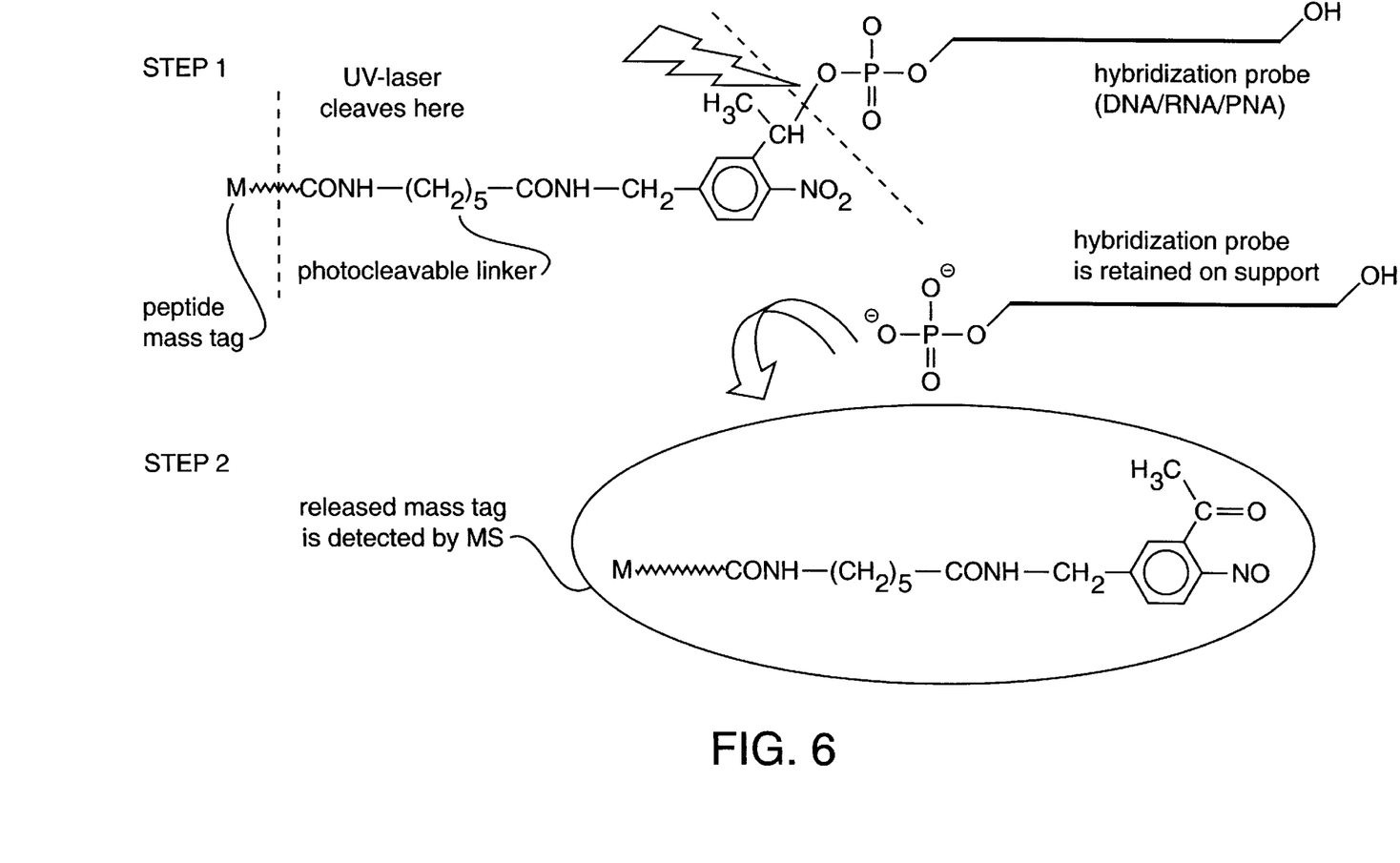
FIG. 6 schematically shows the detection of a peptide marker of an oligonucleotide conjugate by mass spectrometry.
Figure 7:
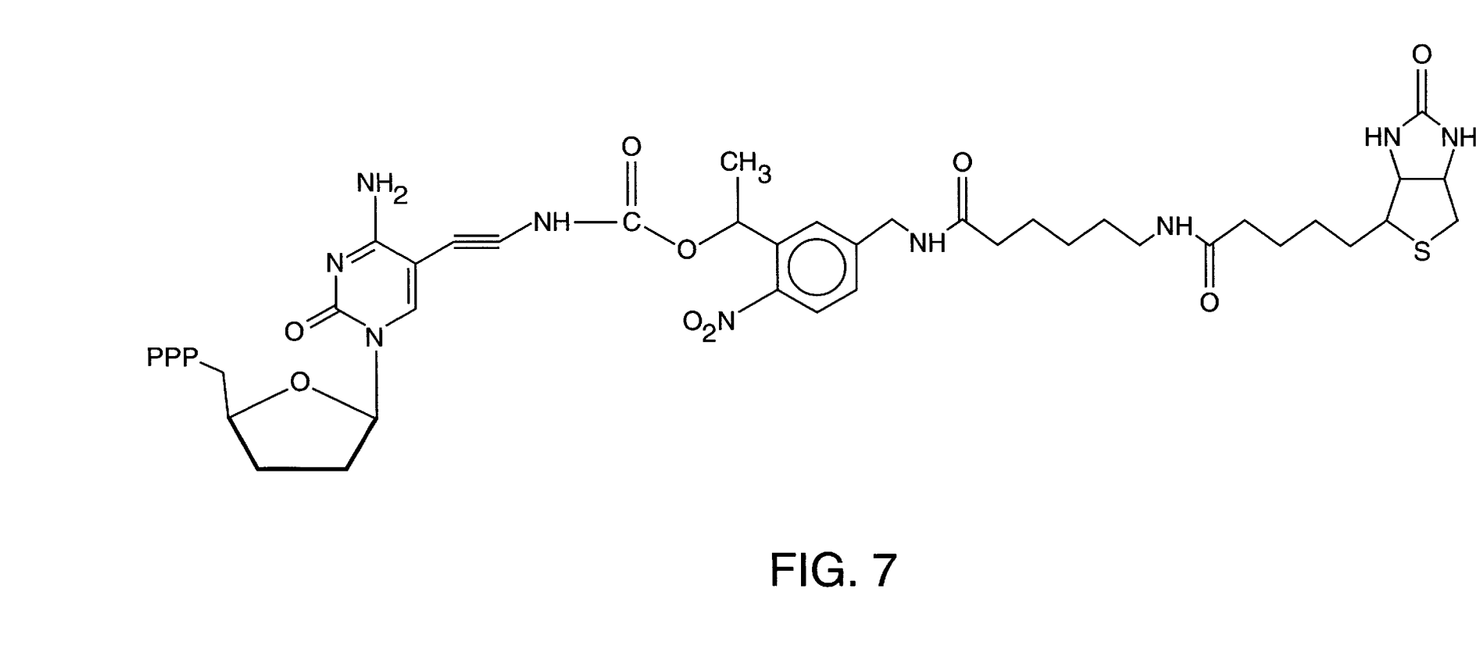
FIG. 7 shows one embodiment of a photocleavable nucleotide of the present invention.
Figure 8A:
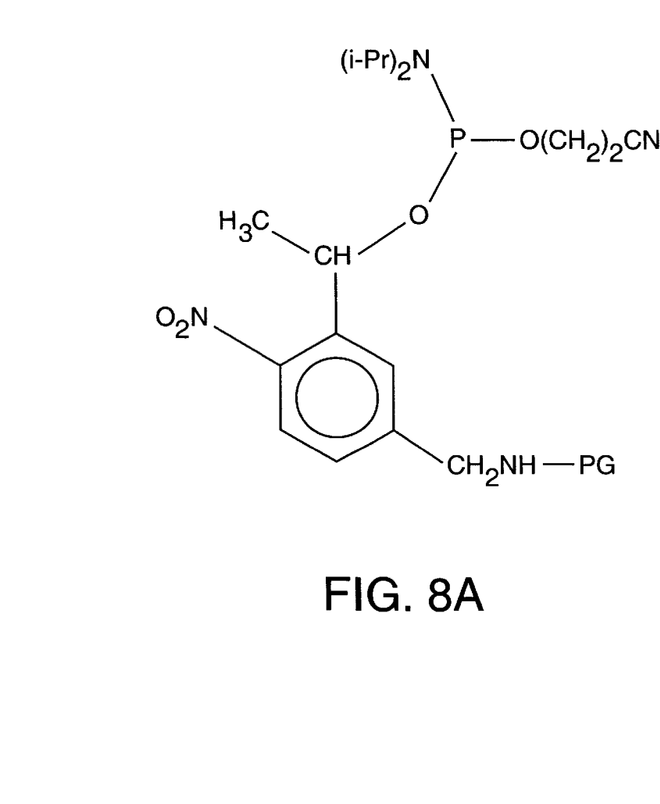
FIG. 8 shows two compounds of FIG. 7 where the protecting group is indicated generically as "PG".
Figure 8B:
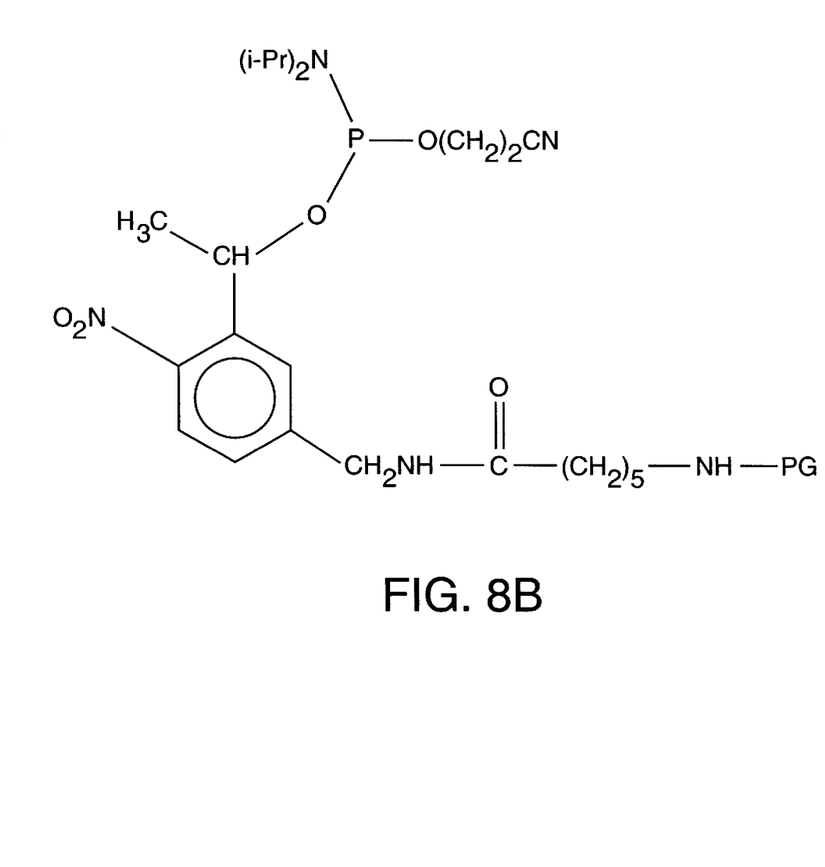

The present invention contemplates the detection of markers, including but not limited to peptide markers. In one embodiment, the present invention contemplates detection by mass spectrometry (e.g. MALDI-MS). In one embodiment, the DNA moeity of the mass marker is hybridized to an immobilized target DNA single strand. The bond between the hybridization probe and the mass tag is then cleaved by the UV-MALDI desorption laser pulse (FIG. 6) and the released mass tag (e.g. an octapeptide mass tag) is detected in the mass spectrum indicating the presence of the complementary sequence of its hybridization probe. This method potentially offers both higher sensitivity compared to the direct detection of the DNA hybridization probe and is less prone to signal degradation due to metastable fragmentation and cation adduct formation. Furthermore, it allows for simultaneous detection of several target sequences, since peptide mass markers can be readily synthesized with easily resolvable mass differences.

F. Photocleavable Nucleotides

The present invention also contemplates photocleavable nucleotides (PC-nucleotides). Using these PC-nucleotides, photocleavable tags (PC-tags) can be enzymatically incorporated into an oligonucleotide through a wide range of enzyme based methodologies for the synthesis and modification of DNA/RNA. These include PCR, terminal deoxynucleotidyl transferase (single labeling or tailing at the 3'-end) and nick translation reaction or replacement synthesis using T4 DNA polymerase (multiple label incorporation). For RNA labeling, appropriate polymerases, such as SP6, T7 and T3 polymerases can be used. Alternatively, T4 RNA ligase can be used to join 3'-labeled (deoxy)nucleotide 5'-monophosphate to target RNA. Dideoxy-PC-nucleotides can be used to end-label the products of polymerase based sequencing reactions thereby facilitating MALDI-MS based sequencing.

Experimental

The following examples serve to illustrate certain preferred embodiments and aspects of the present invention and are not to be construed as limiting the scope thereof.

In the experimental disclosure which follows, the following abbreviations apply: eq (equivalents); $\mu$ (micron); M (Molar); $\mu$M (micromolar); mM (millimolar); N (Normal); mol (moles); mmol (millimoles); $\mu$mol (micromoles); nmol (nanomoles); g (grams); mg (milligrams); $\mu$g (micrograms); ng (nanograms); L (liters); ml (milliliters); $\mu$l (microliters); cm (centimeters); mm (millimeters); $\mu$m (micrometers); nM (nanomolar);° C. (degrees Centigrade); PBS (phosphate buffered saline); TLC (thin layer chromatography); HPTLC (high performance thin layer chromatography); HPLC (high pressure liquid chromatography); U (units); d(days).

All chemicals used in the synthesis were purchased from Aldrich Chemical Co. (Milwaukee, Wis.), unless otherwise indicated. Biotinamidohexanoic acid NHS ester was purchased from Sigma (St. Louis, Mo.), digoxigenin-X-NHS ester (digoxigenin-3-O-methylcarbonyl-(-aminocaproic acid N-hydroxysuccinimide ester) was obtained from Boehringer-Mannheim (Indianapolis, Ind.) and tetramethylrhodamine-X-NHS ester (6-tetramethylrhodamine-5-(and-6)-carboxamidohexanoic acid succinimidyl ester, TAMRA-X-NHS) was from Molecular Probes (Eugene, Oreg.). Fmoc-NHS and N-Fmoc-6-aminocaproic acid were from Novabiochem (La Jolla, Calif.). 1H NMR spectra were recorded in CDCl3 on a Varian Unity Plus (Palo Alto, Calif.) spectrometer at 400 MHz with chemical shifts ((, ppm) reported relative to a tetramethylsilane internal standard. Oligonucleotide synthesis was performed on an Applied Biosystem DNA/RNA synthesizer, model 392 (Foster City, Calif.). Samples were irradiated with a Blak Ray XX-15 UV lamp (Ultraviolet Products Inc., San Gabriel, Calif.) at a distance of 15 cm (emission peak 365 nm; 300 nm cut-off; intensity 2.3 mW/cm2@365 nm). UV-VIS spectra were recorded on a Shimadzu 2101PC spectrophotometer (Columbia, Md.). HPLC analysis was performed on a Waters (Milford, Mass.) system consisting of a U6K injector, 600 Controller, Novapak C18 (3.9×150 mm) column and a 996 photodiode array detector. Buffer A: 0.1 N triethylamine acetate, pH=7.0; buffer B: acetonitrile. Elution was performed using a linear gradient (8–50%) of buffer B in buffer A over 45 minutes at a 1 ml/min. flow. Preparative purifications were achieved on a Waters Novapak C18 RCM cartridge (8×100 mm) using conditions as specified above, except for flow rate, which was increased to 2 ml/min. Fractions were then analyzed by analytical HPLC, fractions pooled and freeze-dried. No special precautions were necessary to protect the reagents and the labeled oligonucleotides from light.

EXAMPLE 1

This example describes the synthesis of 5-N-Fmoc (aminomethyl)-1-(2-nitrophenyl)-ethanol (FIG. 2B, compound 4). As shown in FIG. 2A, this compound can be obtained from 5-bromomethyl-2-nitroacetophenone (compound 1) through a quarternization reaction with hexamethylenetetramine and decomposition of the resulting quaternary salt (compound 2) under acidic conditions. Crude 5-aminomethyl-2-nitroacetophenone hydrochloride (2.5 mmole) was resuspended in 12 ml of methanol and cooled in an ice bath. 48 mg (1.26 mmole, 2.0 eq.) of sodium borohydride was added in small portions with continous stirring during 10 minutes. Subsequent portions of borohydride (30 mg each) were added to reaction mixture until TLC showed complete conversion (FIG. 2, compound 3). The reaction was quenched by addition of 10 ml acetone. 10 ml water was added and the reaction mixture was concentrated under vacuum to approximately 10 mL. 10 ml of acetonitrile was added and the pH of the resulting solution was adjusted to 8.5 using 1N HCl. Fmoc-NHS (1.03 g; 3 mmole, 1.2 eq. in acetonitrile (10 ml) was added slowly during 15 minutes, the pH being adjusted to 8.5 with triethylamine. The reaction mixture was stirred for an additional 1 hour, then it was acidified to pH=3 and extracted with chloroform. The organic layer was dried over anhydrous sodium sulphate and evaporated, yielding 1.4 g of compound 4 as yellow oil, which was purified on a silica gel column using a step gradient (0–2%) of methanol in chloroform. The product was isolated at 1% of MeOH. Yield ~720 mg (69%) 1H NMR (CDCl3+CD3OD): 1.57–1.52 (d, 3H), 2.39 (s, 1H), 4.17–4.19 (m, 1H), 4.39–4.47 (d–d, 2H), 5.34–5.36 (q, 1H), 5.83 (s-br, 1H), 7.17–7.19 (d, 1H), 7.21–7.30 (t, 2H), 7.36–7.40 (t, 2H), 7.55–7.57 (d, 2H), 7.69 (s, 1H), 7.73–7.75 (d, 2H), 7.83–7.85 (d, 1H).

EXAMPLE 2

This example describes the synthesis of compound 5 (FIG. 2B). This reaction was carried out as for compound 4 (See Example 1), except N-Fmoc-6-aminocaproic acid NHS ester was used instead of the Fmoc-NHS. To the solution of compound 3 (5.3 mmol in 40 ml acetonitrile:H2O, 1:1, pH=8.5) a solution of N-Fmoc-6-aminohexanoic acid NHS ester (2.9 g; 1.2 eq.) in 20 ml of dioxane was added during 15 minutes. After work-up, the crude product was purified on a silica gel column using step gradient of methanol in chloroform (0–3%), product (compound 5) being eluted at 2% methanol. Yield ~2.03 g (72%). Rf=(CHCl3: MeOH, 95:5, v:v) 1H NMR (CDCl3+CD30D): 7.79–7.77(d, 1H), 7.72–7.67(m, 3H), 7.60–7.50(d, 2H), 7.35–7.31(t, 2H), 7.27–7.19(m, 3H), 6.42–6.37(app. t, br, 1H), 5.37–5.33(q, 1H), 5.16–5.08(t, br, 1H), 4.46–4.41(m, 2H), 4.33–4.30(d, 2H), 4.15–4.10(t, 1H), 3.14–3.09(q, 2H), 2.23–2.18(t, 2H), 1.67–1.59(m, 2H), 1.48–1.42(m, 3H), 1.35–1.28(m, 2H).

EXAMPLE 3

This example describes the synthesis of yet another photocleavable aminotag phosphoramidite of the present invention, namely 5-N-Fmoc-(aminomethyl)-1-(2-nitrophenyl)ethyl-2-cyanoethyl-N,N-diisopropylamino-phosphoramidite (compound 6, FIG. 2B). For this reaction, compound 4 (200 mg, 0.52 mmole) was dried in vacuo over P2O5 for 5 hrs. 3 ml of anhydrous acetonitrile was injected through septum, followed by N,N-diisopropylethylamine (350 µl, 2.08 mmole, 4 eq.) and finally cyanoethoxy-N,N-diisopropylchlorophosphine (0.52 mmole, 117 µl, 1 eq.). The reaction mixture was stirred at RT for 1 hr then another 0.5 eq. of phosphine was added. After 2 hours the reaction mixture was treated with 1 ml of ethyl acetate and worked-up between aq. NaCl and dichloromethane. The organic layer was washed with water, dried over sodium sulphate and evaporated. Product was purified on silica gel column using a step gradient of ethyl acetate in hexane (0–30%) containing 0.2% of triethylamine. Product was isolated at 22% of ethyl acetate, yielding 130 mg of compound 6 (42%). Rf (hexane:ethyl acetate:Et3N, 45:45:10, v:v:v) 0.80 and 0.86 (two diastereoisomers). ESI-MS M+=619.3 (+H) (618.26 calculated). Elemental analysis: CHN %(calculated); C64.03(64.07); H6.23(6.35); N8.76(9.06). 1H NMR (CDCl3): 7.88–7.84(m, 1H), 7.77–7.27(m, 3H), 7.60–7.55 (m, 2H), 7.40–7.34 (m, 2H), 7.30–7.24(m, 3H), 5.67(t, 1H), 5.55–5.49(q, 1H), 4.45–4.37(m, 4H), 4.24–4.16 (m,1H), 3.87–3.79(m, 1H), 3.65–3.58(m, 2H), 3.48–3.42(m, 1H), 2.62–2.40(m, 2H), 1.55–1.53(d, J=6.8 Hz+s, 4H), 1.19–1.08(d+d+d, J=6.8 Hz, 12H), 0.89–0.85(d, J=6.8 Hz, 3H).

EXAMPLE 4

This example describes the synthesis of an oligonucleotide comprising a photocleavable aminotag phosphoramidite, namely Compound 7 (FIG. 2B). This compound was prepared from compound 5 (1.0 g; 1.92 mmol) N,N-diisopropylethylamine (1.3 ml; 4 eq.) and cyanoethoxy-N,N-diisopropylchlorophosphine (1.5 eq.) in 12 ml acetonitrile using a procedure similar to that described for compound 6. Product was purified on a silica gel column using step gradient of ethyl acetate in hexane (10–70%, v/v) containing 0.8% triethylamine. Product was isolated at 50% ethyl acetate as two diastereoisomers (Rf=0.69, 0.61; AcOEt : hexane : Et3N, 8:1:1, v/v). Yield ~580 mg (41%). ESI-MS, M+=731.2 (731.3, calculated); elemental analysis C 65.34 (64.01) H 6.65(6.89) N 10.08(9.57) (calculated) 1H NMR: 7.84–7.82(d, J=8.4, 1H), 7.72–7.69 (m, 3H), 7.57–7.52 (m, 2H), 7.37–7.32(m, 2H), 7.29–7.25(m, 3H), 6.73–6.65(t, J=6 Hz, 1H), 5.49–5.44(q, 1H), 5.10–5.00(t, 1H), 4.48–4.30(m, 4H), 4.20–4.05(m, 2H), 3.50–3.45(m, 2H), 2.66–2.64(m, 2H), 2.22–2.16(t, 2H), 1.54–1.48(d, J=6.0 Hz, 4H), 1.24–1.20(m, 6H), 1.16–1.13(d, J=6.4 Hz, 4H), 1.09–1.05(d, J=6.8 Hz, 4H)

EXAMPLE 5

This example describes the syntheses of 5'-PC-amino-olignucleotides. The reaction was carried out using a commercially available synthesizer in the Trityl-On mode. Coupling efficiency for PC-aminotag phosphoramidites was determined by HPLC analysis of several sequences and found to be in the range 95–98%. Standard cleavage and deprotection procedures were used. The composition of 5'-PC-amino-(dT)$_7$ and 5'-PC-amino-X-(dT)$_7$ was verified before and after photocleavage reaction by MALDI-TOF: 5'-PC-amino-(dT)$_7$-2326.3 (uncleaved) 2,148.4 (cleaved); 5'-PC-amino-X-(dT)$_7$ 2,438.4 (uncleaved) 2,147.2 (cleaved). Control 5'-phosphorylated sequences were synthesized using the chemical phosphorylation reagent Phosphalink" (Applied Biosystem, Foster City, Calif.) according to the manufacturer's instructions.

EXAMPLE 6

This example describes the reaction of the oligonucleotides of Example 5 with marker molecules. Crude 5'-PC-amino-d(T)$_7$ or 5'-PC-amino-X-d(T)$_7$ (5.0 OD) was dissolved in 200 µl of 0.1 N NaHCO$_3$ (pH=8.5). To this solution was added 100 µl of the NHS ester (biotin, digoxigenin or rhodamine) solution in anhydrous DMF (10 mg/ml). The solution was incubated overnight at room temperature, then it was purified by gel filtration (Sephadex G-25, NAP-10 column, Pharmacia, Piscataway, N.J.), freeze dried and purified to homogeneity on RP HPLC. For photocleavage studies, a solution of 0.2 OD of oligonucleotide in 50 μl of H$_2$O was irradiated for 5 minutes in clear polypropylene microcentrifuge tube and a 20 μl aliquot was then analyzed by HPLC.

EXAMPLE 7

This example describes reactions with activated supports. Two oligonucleotides, 44-mer(5'-H2N-PC-GGC-CGC-TAC-CTC-TCA-(CCA)6-CTG-ATG-AGC-T-3' SEQ ID NO: 2) and 35-mer (5'-H2N-PC-CAT-CAG-(TGG)6-TGA-GAG-GTA-GC-3' SEQ ID NO: 3) were synthesized at 0.2 μmol scale with 5'-PC-aminotag modifier. These were cleaved and deprotected using standard procedures (28% NH3, 1 hr RT, 18 hrs 55° C.) and then freeze-dried. 6-aminohexanoic acid-NHS agarose (100 mg) (Sigma, St. Louis, Mo.) was suspended in 300 μl of water, vortexed briefly and spin-filtered using a 0.22 μm Ultrafree MC filter (Millipore, Bedford, Mass.), then resuspended in 300 μl of water. Crude 5'-PC-amino-oligonucleotide (10.0 OD) was added to a suspension of activated agarose, followed by 40 μl of 1M NaHCO3. The mixture was vortexed at room temperature for 1 hour, spin-filtered and washed with 100 μl of wash buffer (2M NaCl, EDTA, pH=8.0). Finally, the beads were resuspended in 300 μl of wash buffer and irradiated with near UV light for 5 minutes. After irradiation, the suspension was spin-filtered and the beads were washed with wash buffer (100 μl). The combined filtrates were then desalted on a NAP-10 column, analyzed by UV absorption spectroscopy and by denaturing PAGE.

EXAMPLE 8

This example describes the detection of a peptide mass marker. All DNA syntheses were performed on an Expedite 8909 synthesizer (PerSeptive Biosystems, Framingham, Mass.) using phosphoramidite chemistry at either 0.2 or 1.0 μmol scale. For the preparation of photocleavable peptide-DNA mass markers, DNA was assembled in the synthesizer at 1.0 μmol scale and modified on the 5μ-end with PC-Aminotag phosphoramidite. The Fmoc protective group was then removed by brief treatment with tetramethylguanidine, the support was washed with acetonitrile, dried and coupled with activated, Fmoc protected peptide for 2 h. The support was washed with DMF and acetonitrile, dried and then deprotected with ammonia and freeze-dried. The conjugate was purified to homogeneity using RP-HPLC. For this presentation 3 different mass markers were synthesized (see Table 1).

Target DNA was synthesized on DMT-C27 beads (Penninsula Laboratories, Calif.). An aliquot containing approximately 4 nmol of target DNA was taken from the bead suspension and mixed with 10 pmol of the PC mass markers. Hybridization was carried out in hybridization buffer (25 mM NaCl, 20 mM Tris-HCl, 10 mM MgCl$_2$, pH=7.5) under the following conditions: denaturation: 72° C., 10 min., annealing: 72–37° C. over 30 min. Samples were incubated for an additional 30 min. at 37° C., centrifuged, washed with ice-cold water (3×100 μl) and resuspended in 50 μl water.

MALDI-MS measurements on immobilized DNA target sequences were carried out on a Vision 2000 reflectron-TOF mass spectrometer: ($U_{acc}$=5 kV, eq. flight path length 1.7 m, N$_2$ laser, λ=337 nm, τ=3 ns, SEM detector). Solution spectra were obtained on a laboratory built linear TOF-MS instrument equipped with delayed ion extraction ($U_{acc}$=25 kV, equivalent flight path length 12.1 m, Nd:YAG laser, λ=355 nm, τ=5 ns, additional Er:YAG laser, λ=2.94 pm, τ=80 ns, MCP detector) 3-hydroxypicolinic acid and 2,5-dihydroxybenzoic acid were used as matrices for UV-MALDI measurements; for IR-MALDI measurements, succinic acid was used. For measurements on immobilized DNA, a 0.5–1 μl aliquot of the bead suspension was codeposited on the target with 1–2 μl of matrix solution (dried droplet preparation).

In UV-MALDI mass spectra obtained from solutions of each of the mass markers, signals corresponding to the released peptide mass tag, the cleaved DNA and the intact conjugate were observed. In control experiments with IR-MALDI, only a signal corresponding to the intact mass marker and a very weak signal corresponding to the cleaved DNA sequence are detected, while signals of the peptide mass tag are absent. This proves the postulated photocleavage mechanism.

Signals corresponding to mass tags released from mass markers hybridized to immobilized DNA target sequences were readily obtained in Uv-MALDI. In a competition experiment, an equimolar mixture of the 3 mass markers was incubated with beads presenting a DNA sequence complementary to the hybridization probe regions of one of them. Only the mass tag corresponding to the target sequence was detected in UV-MALDI mass spectra obtained from these beads, demonstrating the selectivity of hybridization.

In a different experiment evaluating the possibility of multiplex detection of several target sequences an immobilized strand containing the three target sequences with two nucleotides in between was incubated with an equimolar solution of the 3 mass markers. Signals of all three mass markers were detected in a UV-MALDI mass spectrum obtained from these beads. Relative signal intensities were found not to vary with the arrangement of the target sequences within the immobilized strand.

TABLE 1

| # | Composition Of Mass Marker | | Mass Tag (M + H)$^+$ | Intact Mass Marker (M + H)$^+$ |
|---|---|---|---|---|
| 1 | H$_2$N-GRALGVFV-PC-5'-CAC-GTA-CAG-GAT-GTA-CAG-3' | SEQ ID NO: 4 | 1095.4 Da | 6707.0 Da |
| 2 | H$_2$N-GRALGVFL-PC-5'-TCG-AGA-GGT-ACA-TCG-TG-3' | SEQ ID NO: 5 | 1109.4 Da | 6438.8 Da |
| 3 | H$_2$N-GRALGVFF-PC-5'-AAG-CGG-TAC-GAG-TAG-CA-3' | SEQ ID NO: 6 | 1143.4 Da | 6490.9 Da |

What is claimed is:

1. A composition, comprising a photocleavable aminotag phosphoramidite selected from the group consisting of compounds 6 and 7 of FIG. 2.

2. The composition of claim 1, wherein said photocleavable aminotag phosphoramidite is incorporated at the 5' end of an oligonucleotide.

3. The composition of claim 2, wherein said oligonucleotide is immobilized to a surface via the 3'-end of said oligonucleotide.

4. The composition of claim 2, wherein said oligonucleotide is immobilized via said aminotag to an activated surface.

5. The composition of claim 4, wherein said activated surface comprises activated agarose.

6. The composition of claim 3, wherein said surface is the surface of a bead.

7. The composition of claim 2, wherein a marker molecule is linked to said aminotag phosphoramidite under conditions such that an Fmoc protecting group is removed from said aminotag phosmhoramidite.

8. The composition of claim 7, wherein said marker molecule is selected form the group consisting of activated polypeptides, activated biotin, activated digoxigenin, and activated tetramethylrhodamine.

9. The composition of claim 7, wherein said marker is detectable by spectrometry.

10. The composition of claim 9, wherein said marker is detectable by mass spectrometry.

11. The composition of claim 6, wherein said bead is a glass bead.

12. The composition of claim 11, wherein said glass bead is controlled pore glass.

* * * * *

SEQUENCE LISTING

<160> NUMBER OF SEQ ID NOS: 6

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: synthetic

<400> SEQUENCE: 1
tcgagaggta catcgtg                                                    17

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: synthetic

<400> SEQUENCE: 2
cggccgctac ctctcaccac caccaccacc accactgatg agct                       44

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: synthetic

<400> SEQUENCE: 3
ccatcagtgg tggtggtggt ggtggtgaga ggtagc                                36

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: synthetic

<400> SEQUENCE: 4
cacgtacagg atgtacag                                                   18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: synthetic

<400> SEQUENCE: 5
tcgagaggta catcgtg                                                    17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: synthetic

<400> SEQUENCE: 6
aagcggtacg agtagca                                                    17